(12) United States Patent
Wohlstadter et al.

(10) Patent No.: US 7,008,796 B2
(45) Date of Patent: Mar. 7, 2006

(54) ASSAY SONICATION APPARATUS AND METHODOLOGY

(75) Inventors: Jacob N. Wohlstadter, Rockville, MD (US); James Wilbur, Germantown, MD (US); George Sigal, Rockville, MD (US); Mark Martin, Rockville, MD (US); Alan Fischer, Cambridge, MA (US); Larry R. Helms, Germantown, MD (US); Ramin Darvari, Waltham, MA (US)

(73) Assignee: MesoScale Technologies, LLC., Gaithersburg, MD (US)

( * ) Notice: Subject to any disclaimer, the term of this patent is extended or adjusted under 35 U.S.C. 154(b) by 706 days.

(21) Appl. No.: 10/152,234

(22) Filed: May 21, 2002

(65) Prior Publication Data

US 2002/0137234 A1    Sep. 26, 2002

Related U.S. Application Data

(62) Division of application No. 08/932,985, filed on Sep. 18, 1997, now Pat. No. 6,413,783.

(51) Int. Cl.
   *G01N 21/76* (2006.01)

(52) U.S. Cl. .................. 436/172; 310/311; 366/108; 366/109; 366/110; 366/111; 366/112; 366/113; 366/114; 366/116; 366/117; 366/118; 366/127; 204/400; 204/403; 422/20; 422/52; 422/57; 422/128; 435/7.1; 435/287.1; 435/287.2; 435/288.7; 435/808; 435/7.9; 436/517; 436/518; 436/524; 436/805

(58) Field of Classification Search ................ 310/311; 366/108–114, 116–118, 127; 204/400, 403; 422/52, 57, 20, 128; 435/7.1, 7.9, 287.1, 435/287.2, 288.7, 808; 436/172, 517, 518, 436/524, 805

See application file for complete search history.

(56) References Cited

U.S. PATENT DOCUMENTS

| | | | |
|---|---|---|---|
| 4,114,194 | A | 9/1978 | Walter |
| 4,575,485 | A | 3/1986 | Sizto et al. |
| 5,247,954 | A | 9/1993 | Grant et al. |
| 5,589,136 | A | 12/1996 | Northrup et al. |
| 5,674,742 | A | 10/1997 | Northrup et al. |

FOREIGN PATENT DOCUMENTS

| | | |
|---|---|---|
| EP | 0337690 A1 | 10/1989 |
| JP | 02 312591 | 12/1990 |
| WO | WO 97/33176 | 9/1997 |
| WO | WO 98/12539 A | 3/1998 |

*Primary Examiner*—Christopher L. Chin
(74) *Attorney, Agent, or Firm*—Kramer Levin Naftalis & Frankel LLP; Barry Evans, Esq.

(57) ABSTRACT

An assay apparatus includes a cell with a working electrode and a sonicating device structurally coupled to the cell for sonication the contents of the cell.

13 Claims, 7 Drawing Sheets

ASSAY SONICATION APPARATUS AND METHODOLOGY

This application is a divisional of U.S. application Ser. No. 08/932,985, filed Sep. 18, 1997, now U.S. Pat. No. 6,413,783, which application is hereby incorporated in its entirety by reference.

REFERENCE TO PUBLICATIONS AND CORRESPONDING APPLICATIONS

The following published PCT Applications are hereby incorporated in their entirety by reference: U.S. No. 92/00982 (WO 92/14138); U.S. No. 92/00992 (WO 92/14139); and U.S. No. 96/03190 (WO 96/28538).

The following commonly owned and copending U.S. and PCT Applications, filed on even date herewith are incorporated in their entirety by reference: U.S. patent application Ser. No. 08/932,110 filed Sep. 17, 1997 entitled MULTI-ARRAY, MULTI-SPECIFIC ELECTROCHEMILUMINESCENCE TESTING and PCT Application No. PCT/US97/16942 filed Sep. 17, 1997 entitled MULTI-ARRAY, MULTI-SPECIFIC ELECTROCHEMILUMINESCENCE TESTING (WO 98/12539).

BACKGROUND OF THE INVENTION

Diagnostic tests upon liquid samples and diagnostic tests utilizing liquids are in widespread use in medical technology, environmental monitoring devices, and commercial applications. A significant impediment to the utilization of many diagnostic testing processes has been the impractical delay required for chemical reactions in such processes to proceed to a meaningful completion. It is not uncommon for diagnostic chemical reactions occurring in a liquid system to proceed for extended periods of time, e.g., in excess of thirty minutes. Such delay may make certain diagnostic tests entirely unsuitable for situations in which timely results are needed.

In an emergency room, delay in obtaining results from a diagnostic test may delay accurate evaluation of a patient's condition, to the extreme detriment of the patient. Even under less critical circumstances, such as a routine visit to a doctor's office, an hour delay in obtaining results from a diagnostic test may hinder a doctor's diagnosis and treatment of a patient during a single consultation. Any delay in treatment could result in harm to the patient. At the least, an extended delay in obtaining test results may necessitate an additional follow-up consultation and office visit, thereby increasing the overall cost of treatment to the patient. In the laboratory, the slow chemical reaction time of a diagnostic test may significantly reduce the efficiency of research efforts and burden researchers. Further, time-consuming diagnostic testing in industrial chemical processes may dramatically increase manufacturing costs and reduce production volume.

To avoid the above-described consequences, apparatus and methodology for increasing the speed of diagnostic testing processes are greatly desired, especially in connection with assays that incorporate a binding reaction, e.g., immunoassays, nucleic acid hybridization assays, and receptor-ligand binding assays. It would be particularly useful to increase the reaction rate in assays utilizing binding reactions that involve the binding of components of a solution to reagents located at a solid-phase support. Such assays should provide precise, quantitative results and be highly sensitive. In addition, it is also desirable that apparatus for conducting diagnostic test assays be small, portable, low cost, robust, and easy to operate. The above considerations are especially important in the field of Point-of-Care (POC) medical diagnostic testing (e.g., testing done at home, at a hospital bedside, in an emergency room, or in a doctor's office).

It is believed that the rate of a binding reaction depends upon the mass transport rate of the reagents involved. For binding reactions that occur at a solid-phase support, the rate at which molecules in solution bind to reagents located at a solid-phase surface may be limited by the rate of mass transport of the molecules to the surface. When such systems are not subject to active mixing, molecules in solution reach the solid-phase surface primarily by diffusion through the solution. It has been found that diffusion rates are generally too slow to allow binding reactions to approach completion with a 30 minute period. In addition, the presence of small convection currents in the solution, e.g., due to temperature gradients, can cause the rates of a binding reaction to vary considerably and thus be difficult to predict and control.

There have been numerous prior attempts to improve the mass transport of molecules to a solid phase support in a binding reaction system. Considerable efforts have been directed to increasing mass transport rates through the introduction of controlled convection currents, e.g., by vortexing, by using stirring devices, or by passing a solution over a solid-phase surface in a flow cell arrangement. Such approaches commonly utilize relatively expensive and complex mechanical devices, such as solution stirrers or pumps, and, consequently, are not suited for use in an assay device that is small in size, robust, inexpensive to manufacture, and easy to use.

Also, a liquid ultrasonication bath to promote mixing has been described in U.S. Pat. No. 4,575,485 (Sizto et al.). Sizto et al. mention a container, holding a volume of assay medium and a "dip-stick" immersed in the medium, submersed in the bath of a conventional liquid-bath ultrasonic cleaning device. Ultrasonic vibrations from the shell of the cleaner bath are liquid-coupled to the container. The vibrations traveling through the liquid of the cleaner bath dissipate in the volume of the bath and reflect off of the container material and off of the shell of the bath. Such liquid-coupling is clearly inefficient and can dissipate considerable amounts of ultra sonic energy.

The exact nature of the ultrasonic vibrations being transmitted to the assay medium and to the dip-stick will significantly depend upon apparatus design and usage conditions. For example, the shape of the container for the assay medium, the shape of the shell of the bath, the position of the container in the bath, the position of the dip-stick in the container, the position of the source of vibrations, the amount of dissolved gas in the liquid in the bath, and the volume of liquid in the bath will each affect the transmission of ultrasonic vibrations. In use, the volume of liquid could easily change due to evaporation, splashing or release of gasses dissolved in the liquid in the bath. All of these may affect the vibration transmission characteristics of the bath.

Since small variations in structure and operational conditions will considerably affect the transmission of ultrasonic energy in a device according to Sizto et al., it can be expected that precise reproduction of particular ultrasonic bath conditions throughout the duration of a particular reaction will be extremely difficult, if not impossible, to achieve. Consequently, it will be extremely difficult, if not impossible to achieve reproducible assay results with such a device. Time-consuming chemical reactions sensitive to ultrasonic energy may not be reproducible at all. In addition, the use by Sizto et al. of a liquid bath ultrasonic cleaner device presents an unnecessary risk of cross-contamination between the bath and the assay medium. Such contamination is likely to cause erroneous assay results.

Further, an apparatus according to Sizto et al. is not particularly suited to commercial application. As a consequence of designedly incorporating a liquid bath, the apparatus of Sizto et al. is relatively large, cumbersome and heavy and consumes considerable electrical power. Such power is required because of the wasteful dissipation of ultrasonic energy in the bath shell, bath liquid, and assay container. Clearly, a device according to Sizto et al. very inefficiently transmits ultrasonic energy to an assay medium in a container and from there to a binding surface. Moreover, the use of an ultrasonication bath is an additional complicated assay step requiring skillful manipulation by a user. As such, an ultrasonication bath is not suitable for use in an integrated, automated assay system or for use by assay technicians that are not highly skilled. Disadvantageously, the ultrasonication bath of Sizto et al. cannot be incorporated into an assay device or assay system that is small, robust, inexpensive, easy to use. The ultrasonication bath would also not be suitable for a disposable device.

Many assay techniques detect the binding of molecules in solution to reagents located at a solid phase. The binding of molecules to reagents on a solid phase can be measured directly, for example, by surface plasmon resonance. Alternatively, by attaching a label to a molecule in solution, the binding of the molecule to a surface can be determined by measuring the amount of label located on the surface. Typical labels used in assays include enzymes, fluorescent molecules, radioactive isotopes, chemiluminescent molecules, electroactive molecules, and colloidal particles. For more description of the field, the reader is referred to *Nonradioactive Labeling and Detection of Molecules*, Kessler, C., ed., Springer-Verlag, Berlin 1992; *The Immunoassay Handbook*, Wild, D., ed., Stackton Press, New York 1994; and Keller, G. H.; Manak, M. M. *DNA Probes,* 2nd Ed., MacMillan Publishers Ltd., London, 1993.

One particularly useful detection technique is electrochemiluminescence (ECL). In ECL, electron transfer reactions at or near an electrode causes a label to adopt an electronically excited state. The excitation level of the label decays through emission of a photon which can be photometrically detected. Derivatives of ruthenium tris-bipyridyl (TAG1) are widely used as ECL labels. Further details regarding ECL detection techniques can be found in Bard et al. (U.S. Pat. No. 5,238,808) and Knight et al., 1994, Analyst, 119:879–890. While ECL monitoring of binding reactions in solution has been described, it is noted that a wide variety of ECL-based binding assays utilize binding reagents located on a solid-phase support. For example, the solid-phase support may consist of a magnetic bead that is deposited on an electrode surface (published PCT WO 92/14138 and Yang, H.; Leland, J.; Yost, D. Massey, R.; Bio/Technology 12 (1994) 193–194). Alternatively, an electrode (e.g., a fibril-polymer composite electrode) may be derivatized so as to provide a solid-phase support, for example, as described in copending U.S. application Ser. No. 08/932,110 filed on even date herewith, and PCT Application No. PCT/US97/16942 (WO 98/12539) filed on even date herewith, both of which are incorporated by reference above.

OBJECTS AND SUMMARY OF THE INVENTION

Therefore, an object of the present invention is to provide apparatus and methodology for increasing the speed of diagnostic testing processes.

Another object of the present invention is to provide sonication apparatus and methodology avoiding the disadvantages suffered by the prior art and increasing the speed of diagnostic testing processes.

Yet another object of the present invention is to provide apparatus for sonicating an assay cell or cartridge used in an electrochemiluminescence assay.

According to an aspect of the present invention, an apparatus for use in carrying out electrochemiluminescence measurements is provided. The apparatus comprises a cell that includes a working electrode, a sonicating device, structurally coupled to the cell, for sonicating the contents of the cell.

According to an aspect of the present invention, an apparatus for use in carrying out electrochemiluminescence measurements is provided. The apparatus includes a cell that includes a working electrode. The apparatus also includes a sonicating device, structurally coupled to the working electrode, for increasing the rate of mass transport of molecules to and/or from the surface of the working electrode.

According to another aspect of the present invention, an apparatus for use in carrying out electrochemiluminescence measurements is provided. The apparatus includes a cell that includes a working electrode, wherein the working electrode is a solid-phase support for binding reagents specific for an analyte of interest. The apparatus also includes a sonicating device, structurally coupled to the cell, for sonicating the contents of the cell.

According to another aspect of the present invention, an apparatus for use in carrying out a plurality of electrochemiluminescence measurements is provided. The apparatus includes a cell, that includes one or more working electrodes, wherein the one or more working electrodes are solid-phase supports for one or more binding domains. The one or more binding domains comprise binding reagents specific for one or more analytes of interest. The apparatus also includes a sonicating device, structurally coupled to the cell, for sonicating the contents of the cell.

According to another aspect of the present invention, an apparatus for use in carrying out electrochemiluminescence measurements is provided. The apparatus includes a cell, that includes a working electrode, and an ultrasonicating device, structurally coupled to the cell, for ultrasonicating the contents of the cell.

According to another aspect of the present invention, an apparatus for use in carrying out electrochemiluminescence is provided. The apparatus includes a cartridge comprising a working electrode, that is a solid-phase support for binding reagents specific for an analyte of interest. The apparatus also includes a cartridge reader that includes a receptacle for the cartridge, a device for correctly positioning the cartridge in the receptacle, an electrical contact to the working electrode, a source of electrical energy for exciting ECL at the surface of the electrode, a light-detection device for measuring the emission of ECL, and a sonicating device, reversibly structurally coupled to the cartridge, for sonicating the contents of the cartridge.

According to still another aspect of the present invention, a method for carrying out electrochemiluminescence measurements is provided. The method includes the steps of introducing a sample comprising an electrochemiluminescent moiety into a cell including a working electrode; sonicating the sample in the cell with a sonicating device structurally coupled to the cell; and applying electrical energy to the electrode to cause the electrochemiluminescent moiety in the sample to luminesce.

According to yet another aspect of the present invention, a method for preparing an electrode in a cell or cartridge for use in electrochemiluminescence measurements is provided. The method includes sonicating the cell or cartridge with a sonicating device structurally coupled to the cell or cartridge so as to remove undesired contaminants from the surface of the electrode and to increase mass transport of desirable reagents to the surface of the electrode.

Other objects, features, and advantages according to the present invention will become apparent from the following detailed description of illustrated embodiments when read in conjunction with the accompanying drawings in which the same components are identified by the same reference numerals.

DETAILED DESCRIPTION OF THE PREFERRED EMBODIMENTS

Figure 1:
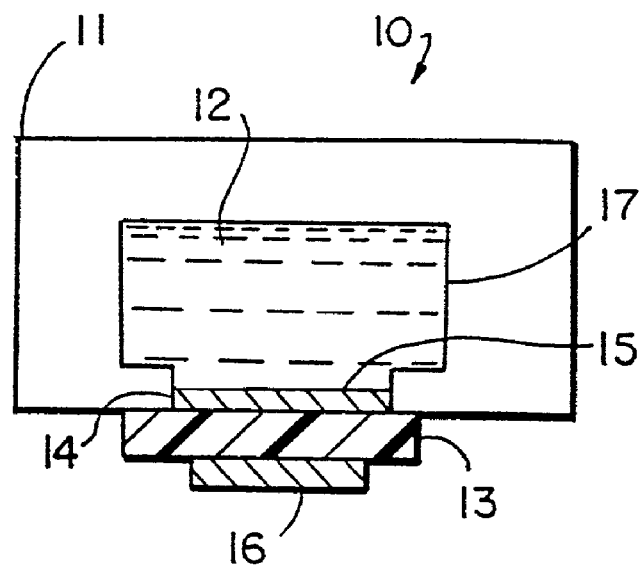
FIG. 1 is a schematic diagram of an assay cell according to an embodiment of the present invention.

In many diagnostic systems wherein binding reactions occur between reagents, improved mixing of the reagents can increase the speed of the reaction. Often, the slow rate of mixing ultimately limits the speed with which a diagnostic test proceeds to completion. Examples of diagnostic assays wherein binding reactions between reagents occur include immunoassays, DNA-probe assays, clinical chemistry tests, receptor-ligand binding assays, and the like. The slow rate of binding kinetics has been an especially limiting constraint in conducting assays that incorporate binding reactions between reagents in solution and reagents present on a solid. Sonication improves the mixing of reagents in solution and the mass transport of reagents in solution to reagents located on or near a surface of a solid. Experiments have proven that sonication of assay reagents dramatically decreases the time required to conduct a binding assay that utilizes a solid-phase support. In the present application, sonication is defined to encompass vibration having a frequency between approximately 100 Hz and 10 MHz. The frequency of sonication ($f_s$) can be sub-divided into the following ranges: low-frequency sonication (100 Hz$\leq f_s \leq$5 KHz), ultrasonication (between 5 KHz$\leq f_s \leq$1 MHz), and ultra-high sonication (1 MHZ$\leq f_s$). The amplitude of the vibrations can be sub-divided into the following ranges: low amplitude sonication (<1 $\mu$m), medium amplitude sonication (1–10 $\mu$m) and high amplitude sonication (>10 $\mu$).

The improved mixing achieved by the present invention finds ready and useful application in both end-point and kinetic assays. In an end-point assay, the concentration or amount of an analyte of interest is determined by measuring how much binding has occurred when the binding reaction has approached completion. We have found that sonication during the course of the binding reaction decreases the time required for the binding reaction to approach completion. In a kinetic assay, the concentration or amount of an analyte of interest is determined by measuring the rate of the binding reaction. Similarly, it has been found that sonication during the course of the binding reaction increases the rate of the binding reaction. The faster binding reaction produces measurable signals in much less time than previously possible. The present invention so greatly accelerates the rates of certain reactions that assays utilizing such reaction may be completed in only a matter of minutes, often in less than three minutes.

The rate of a mass transport-limited binding reaction on a solid support may be a function of both the concentration of the soluble reagent and the mass-transport coefficient for the mass-transfer of that reagent to the solid support. Therefore, it is especially important that the amount, rate, and type of sonication applied during a kinetic assay be carefully controlled and be precisely reproducible. Variations in the mass-transfer coefficients are likely to cause variations in reaction rate among otherwise identical tests and, consequently, render imprecise or entirely unusable results. The use of a sonication device structurally coupled to an assay cell and/or to a solid-phase support enables the conduct of kinetic binding assays that are quick, quantitative, highly sensitive, and reproducible.

It has been found that for sandwich immunoassays using capture antibodies located on a solid-phase support, the binding reaction can take more than ½ hour to reach completion, even when vortexing is used to increase mass transport to the solid-support surface. This time scale is typical of many highly sensitive solid-phase binding assays, such as ELISA and RIA. Unexpectedly, we found that sonication of reagents reduced the time required for completion of these binding reactions to a matter of minutes. The apparatus and methodology of the present invention is not limited to immunoassays and will be useful for a wide variety of binding interactions (e.g., nucleic acid hybridization, antigen-antibody, receptor-ligand, enzyme-substrate, etc.). The invention is advantageously employed in ECL assays using binding domains located on a working electrode (i.e., said working electrode also functioning as a solid-phase support), for example, as described in copending U.S. application Ser. No. 08/932,119 filed on even date herewith, and PCT Application No. PCT/US97/16942 (WO 98/12539) filed on even date herewith, both of which are incorporated by reference above.

Sonication is also advantageously employed in systems where the solid-phase support has a plurality of binding domains, wherein two or more of said binding domains reside on a different location on the solid phase support. In this case obtaining accurate and reproducible results requires that the sample be mixed sufficiently so that all portions of the sample are exposed to all binding domains. Sonication, by increasing mass transport not only increases the rate of the reaction but can also make the reactions between sample, reagents, and binding domains more uniform.

Sonication is also advantageously employed in systems where the solid-phase support has a plurality of binding domains, some or all of said binding domains being specific for different analytes. Obtaining accurate and reproducible results requires that the sample be uniformly exposed to the binding domains on the support.

Sonication can have beneficial effects besides increasing the rate of the binding reaction. For example, the rate of color development in an ELISA assay may be limited by the rate at which the enzyme substrate travels to the solid surface and the rate of which the enzyme product travels away from the solid surface. Similarly, many chemiluminescent reactions used in assays are initiated by the reaction of chemiluminescent labels, bound to a solid-phase support, with co-reagents present in solution and, thus are accelerated by sonication. Also subject to improvement are assays utilizing electrochemical detection methods that require the mass transport of electroactive species to an electrode surface. Apparatus according to the present invention demonstrate a more-than three-fold increase in the ECL signal produced by a solution containing TAG1 and the ECL coreactant tripropylamine (TPA) when the experimental cell is sonicated during the excitation of ECL. The present invention can, therefore, be applied to the more sensitive ECL detection of ECL labels and ECL coreactants.

Sonication will not only increase the rate of mass transport of reagents to a surface of a solid but will also increase the rate of mass transport of reagents, products, byproducts, contaminants, and the like away from the surface. Sonication can be used to increase the rate of displacement reactions, e.g., the displacement by an unlabeled analyte present in a sample of a labeled analyte bound to a binding reagent. Sonication may also be used to increase the rate of desorption of undesired contaminants on a solid-phase support, thus, reducing the amount of interference and non-specific binding produced in a particular assay. Further, sonication may increase the rate of adsorption of desired materials, such as assay reagents or a protective coating, or the like, and increase the rate of desorption of expended or otherwise undesirable materials, such as a protective coating, non-specifically bound reagents, or the like. Sonication may be used to re-suspend particulate contamination, e.g., cell membranes or particulate reagents, that has settled on a surface.

Sonication may also be used in a sample preparation step. For example, sonication may be used to disrupt materials such as biological tissue cells, microorganisms, virus particles and the like, to release components of the materials into the reaction media. Preferably, said sample preparation occurs, in situ, in a measurement cell, e.g., an ECL cell.

Still further, sonication may be used to decrease the time needed to mix two or more solutions to homogeneity, the time needed to dissolve a solid in a solution, and the time needed to rehydrate a dried material. Sonication is also useful in increasing the rate of fluid flow through thin capillaries.

The slow rate of chemical reactions can also be a limiting constraint in conducting assays that incorporate chemical reactions between reagents in solution and/or between reagents in solution and reagents on a solid. Sonication improves the mixing of reagents in solution and the mass transport of reagents in solution to reagents located on or near the surface of a solid. The increased mixing afforded by sonication can dramatically decrease the time required to conduct an assay that utilizes chemical reactions between reagents in solution and chemical reactions between reagents in solution and reagents located on or near a solid support.

The slow rate of binding kinetics can also be a limiting constraint in conducting assays that incorporate binding reactions between reagents in solution. Sonication improves the mixing of reagents in solution and can dramatically decrease the time required to conduct a binding assay in solution.

Sonication may be used for assays that incorporate chemical reactions between reagents in solution and/or between reagents in solution and reagents located on a solid. Sonication may also be used for assays that incorporate binding reactions between reagents in solution.

Sonication may be created by a variety of mechanical and electromechanical devices. Such devices include electric motors with an eccentrically mounted cam, electromagnetic actuators, such as, speakers, crystal oscillators, pendulum devices, solenoids and the like. A preferred device for creating sonication at a frequency and amplitude particularly suitable for the present invention incorporates a piezoelectric material. Piezoelectric materials are generally inexpensive, commonly available, lightweight, and can be induced to sonicate over a wide range of frequencies and amplitudes. Conveniently, piezoelectric sonication devices are usually rather small in size, making them especially useful in desktop and portable devices. Most advantageously, piezoelectric devices may be operated with very small amounts of electrical power. Piezoelectric devices are, therefore, compatible with small, portable, power sources such as batteries. Sonication apparatus according to the present invention are effectively sonicated with piezoelectric devices that consume less than ten watts, and a particular apparatus functions with a piezoelectric device consuming approximately 0.25 watts. A preferred piezoelectric device is a piston-mass device.

It was further discovered that structural coupling of sonicating energy from a sonication generator to a cell containing assay materials is a remarkably efficient design. The most effective structural coupling has proven to be solid contact, e.g. by direct attachment of the sonication generator to the cell or attachment of the sonication generator so that a solid continuum is provided between the sonication generator and the assay cell. By specifically transmitting sonication energy to the assay cell or to a solid-phase support in the assay cell, much less energy is needed as compared to inducing an entire apparatus to sonicate. Careful positioning of the sonication generator allows focused direction of the energy of the contents of the assay cell and lessens the effects of damping by other elements of an assay system. Structural coupling may be reversible (e.g. the sonication generator and the cell may be designed to be connected and unconnected multiple times) or may represent a permanent connection.

It is to be understood that structural coupling of sonication energy can be achieved with many different types of configurations. The structural coupling of sonication energy specifically encompasses the transmission of sonication energy (a) through a solid interface between a sonication generator and an assay medium or binding surface; or (b) from a sonication generator directly to an assay medium or to a binding surface.

It is an important advantage of the present invention that the structural coupling of sonication energy in apparatus according to the present invention can be precisely controlled. Such control of the structural coupling mechanism is readily implemented through precise control of the manufacturing apparatus components and the assembly of same. Each component of the structural coupling mechanism, e.g. the sonication generator, the diaphragm, etc., can be manufactured to precise tolerances. Similarly, the structural coupling mechanism is suitable for precise assembly permitting the construction of multiple apparatuses having virtually identical sonication transmission characteristics. Preferably, sonication assay cells manufactured to precise tolerances use components comprising rigid materials.

The present invention is generally applicable to binding assay systems such as immunoassays, nucleic acid hybridization assays, receptor-ligand binding assays, and the like. Further assays in which the present invention is advantageously employed includes assays that involve the direct detection of an analyte, detection through a competitive binding reaction, or indirect detection, such as sandwich immunoassays, sandwich nucleic acid hybridization assays, detection of enzymatic products and detection of amplification products. Such assays may be homogeneous or heterogeneous and may or may not incorporate a wash step. The present invention is suitable for use with a variety of techniques used to detect binding events, such as ELISA, fluorescence, chemiluminescence, RIA, scintillation proximity, direct optical detection (e.g., SPR), electrochemical detection, and electrochemiluminescence. It has been found that assay systems like these are particularly responsive to sonication directly structurally coupled to the assay cell or to the assay medium. In assays where binding reactions occur in the vicinity of an electrode, sonication of the electrode itself has proven to have an especially beneficial effect in increasing assay reaction rates.

As will be understood by one of ordinary skill in the art, FIGS. 1–7 present simplified cross-sectional diagrams illustrating different assay cell designs that embody principles and useful applications of the present invention. To facilitate concise explanation but wide-ranging application, particular assay cell features and elements needed to perform specific types of assays have been omitted in some or all of the figures. The drawings, and features depicted therein, are not necessarily drawn to scale. Moreover, to further facilitate explanation of the present invention, certain features of the present invention shown in the drawings have been enlarged or reduced in size relative to other features in the same or other drawings.

In addition, description and illustration of specific electrical connections for, and mechanical couplings among, assay cell elements have been omitted to simplify the drawings. The assay cells presented may be incorporated into larger assay device systems or be available as a modular item. As an example, assay cells according to the present invention may advantageously be incorporated into the ECL systems set forth in U.S. Pat. No. 5,061,445 (Zoski et al.), U.S. Pat. No. 5,147,806 (Kamin et al.), and U.S. Pat. No. 5,247,243 (Hall et al.) as well as in copending U.S. application Ser. No. 08/932,110 filed on even date herewith, and PCT Application No. PCT/US97/16942 (WO 98/12539) filed on even date herewith, both of which are incorporated by reference above.

In the following, each assay cell is shown containing a quantity of reagents which are labeled with the term "reagents". Such "reagents" include solid, liquid, and gaseous reagents, as well as solutions, suspensions, gels and other flowable states in which reagents may exist, combinations of any of the foregoing, and the like. Reagents may include the reagents required to perform an assay as well as a sample of unknown composition that is analyzed by an assay. Examples of suitable reagents and assay systems are found in copending U.S. application Ser. No. 08/932,110 filed on even date herewith, and PCT Application No. PCT/US97/16942 (WO 98/12539) filed on even date herewith, both of which are incorporated by reference above.

In a preferred embodiment, the sonication generator is structurally coupled to a solid-phase support at which binding reagents are located. In an especially preferred embodiment, the solid-phase support is an electrode capable of inducing an ECL moiety to luminesce. Preferably, the electrode comprises a fibril-polymer composite material.

FIG. 1 illustrates a particular cross-sectional view of an assay cell 10 according to an embodiment of the present invention. Assay cell 10 comprises a base 11, a diaphragm 13, and a sonication generator 16. Base 11 is shaped to define a cavity 17 and an aperture 14, and is preferably a rigid material. Alternatively, base 11 comprises a flexible material (e.g., base 11 comprises a flexible plastic container or a blister pack). In assay formats that use optical detection techniques (e.g., ECL, fluorescence, chemiluminescence), base 11 is preferably a transparent material, such as acrylic or the like, that allows light generated within cavity 17 to be detected by a detector (not shown) coupled to base 11.

Diaphragm 13 is a solid-phase support for a reagent 15, such as a binding reagent, and preferably is comprised of a thin film or sheet of material. In particular, diaphragm 13 is preferably a fibril-polymer composite material. As shown, diaphragm 13 is coupled to base 11 at aperture 14. Preferably, diaphragm 13 forms a seal with base 11 covering aperture 14.

Sonication generator 16 is a device for sonicating diaphragm 13. Preferably, sonication generator 16 comprises a piezoelectric sonication device. Generator 16 is preferably controlled by a sonication generator controller (not shown) such as an electrical control circuit or the like. Sonication generator 16 is structurally coupled to diaphragm 13 so as to efficiently transmit sonic energy to diaphragm 13 and to reagents 12.

In operation, reagents 12 are introduced into cavity 17. Sonication generator 16 is energized and sonicates diaphragm 13. Diaphragm 13 conducts the sonication energy to cavity 17, and thus to reagents 12 contained therein. The sonication causes reagents 12 to mix, speeding the rate of reaction among reagents 12. The sonication will also increase the rate of mass-transport of reagents, products, byproducts, etc., to and from binding reagents 15 on diaphragm 13, thus, speeding the rate of binding reactions at the solid-phase support. Alternatively, binding reagents 15 may be omitted.

In an alternate embodiment, a non-solid coupling material (not shown) is placed between generator 16 and diaphragm 13. The coupling material may be liquid or gas. It is contemplated that the coupling material may be held in a sealed container, such as a flexible plastic membrane. In another embodiment, the coupling material may comprise a solid piston structure. Sonication energy from sonication generator 16 is structurally coupled via the solid piston structure to diaphragm 13. In a further alternate embodiment, reagent 15 is omitted from the surface of diaphragm and is located on a surface of cavity 17.

Figure 2:
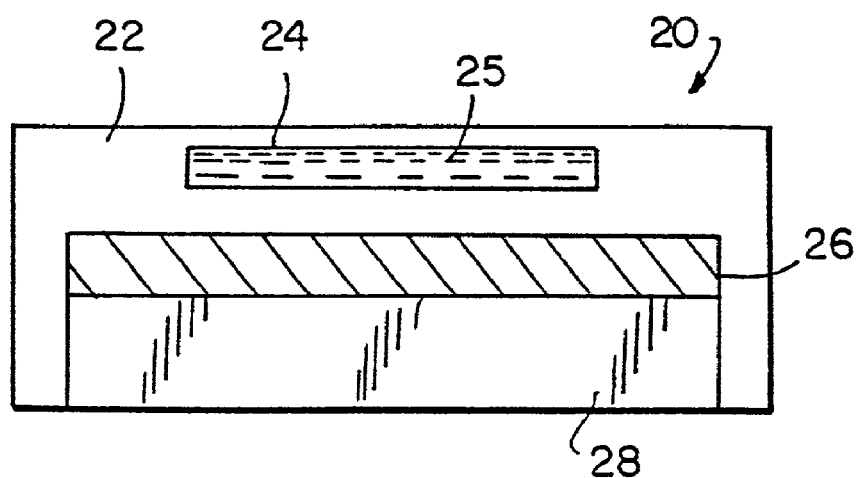
FIG. 2 is a schematic diagram of an assay cell according to another embodiment of the present invention.

FIG. 2 illustrates a particular cross-sectional view of an assay cell 20. Assay cell 20 includes a base 22, a reaction enclosure 24, a sonication device 26, and a device mount 28. Base 22 is preferably a rigid material that surrounds reaction enclosure 24 and structurally couples sonication device 26 to reaction enclosure 24. Alternatively, base 22 comprises a flexible material (e.g., base 22 comprises a flexible plastic container or a blister pack). In assay formats that use optical detection techniques (e.g., ECL, fluorescence, chemiluminescence), base 22 is preferably a transparent material, such as acrylic or the like, that allows light generated within reaction enclosure 24 to be detected by a detector (not shown) coupled to base 22.

Reaction enclosure 24 is preferably a void in base 22 in which assay reagents 25 may be introduced and subjected to sonication to promote mixing and reaction. Alternatively, reaction enclosure 24 may comprise a separate enclosure comprising transparent material that is structurally coupled to base 22. The interior surface of enclosure 24 may be utilized as a solid-phase support for binding reagents and such reagents may be immobilized upon the solid-phase support. Enclosure 24 may have one or more openings therein to connect with passages (not shown) for the introduction and removal of reagents.

Sonication device 26 is a device for sonicating base 22 such that sonication energy will propagate to reaction enclosure 24 and reagents 25 contained therein. Preferably, sonication device 26 comprises a piezoelectric sonication device. Device 26 is preferably controlled by a sonication controller (not shown) such as an electrical control circuit or the like.

Device 26 mounts on device mount 28 which is adapted to securely hold device 26 in close contact with base 22. Although device 26 is shown immediately abutting base 22 and device mount 28, a small space may exist between base 22 and device 26 and/or between device mount 28 and device 26 to allow device 26 to expand and contract or to otherwise move while sonicating.

In an alternate embodiment, a non-solid coupling material (not shown) is placed between device 26 and base 22. The coupling material may be liquid or gas. It is contemplated that the coupling material may be held in a sealed container, such as a flexible plastic membrane. In a further alternate embodiment, device mount 28 may be omitted and device 26 may be attached directly to base 22 (e.g., via adhesives or mounting hardware).

In operation, reagents 25 are introduced into reaction enclosure 24. Sonication device 26 is energized and sonicates base 22. Base 22 conducts the sonication energy to reaction enclosure 24 and thus to reagents 25 contained therein. The sonication causes reagents 25 to mix, speeding the rate of reaction among reagents 25. Where enclosure 24 contains binding reagents or other reagents immobilized on or otherwise located at a solid-phase support, the sonication will also increase the rate of mass-transport of reagents, products, byproducts, etc., to and from the support, thus, speeding the rate of binding reactions at the solid-phase support.

Figure 3:
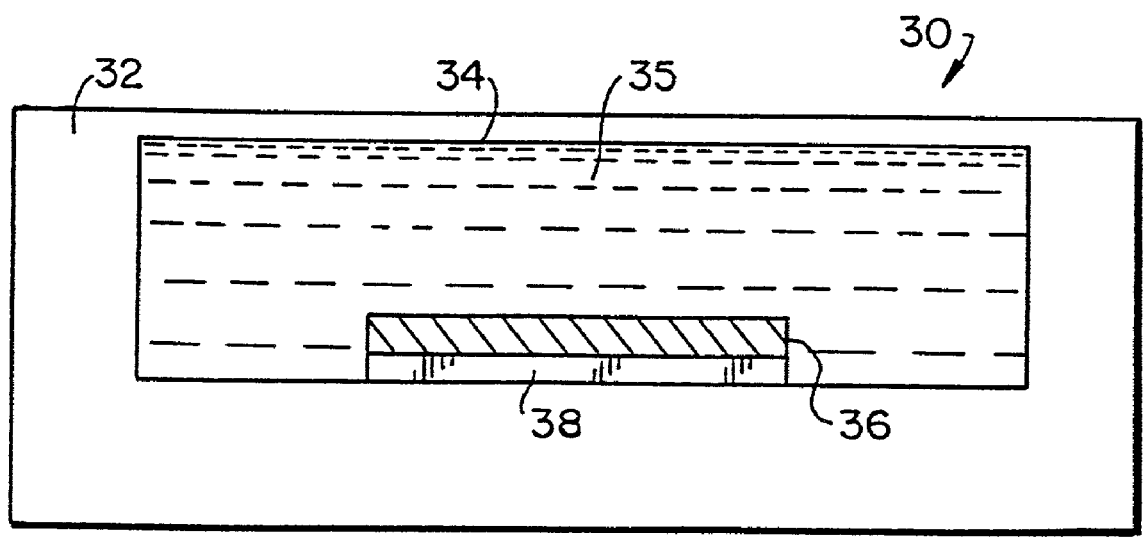
FIG. 3 is a schematic diagram of an assay cell according to another embodiment of the present invention.

FIG. 3 illustrates a particular cross-sectional view of an assay cell 30. Assay cell 30 includes a base 32, a reaction enclosure 34, a sonication device 36, and a device mount 38. Base 32 is preferably a rigid material that surrounds reaction enclosure 34. In assay formats that use optical detection techniques (e.g., ECL, fluorescence, chemiluminescence), base 32 is preferably a transparent material, such as acrylic or the like, that allows light generated within reaction enclosure 34 to be detected by a detector (not shown).

Reaction enclosure 34 is preferably a void in base 32 in which assay reagents 35 may be introduced and sonicated to promote mixing and reaction. Alternatively, reaction enclosure may comprise a separate enclosure, made of a transparent material that is structurally coupled to base 32. Enclosure 34 may have openings (not shown) for the introduction and removal of reagents.

Sonication device 36 is a device for sonicating reagents and/or reaction enclosure 34. Preferably, sonication device 36 may be exposed directly to reagents 35. Alternatively, sonication device 36 may be encased in a protective covering (not shown) that is capable of transmitting sonication energy from device 36 to reagents 35. Sonication device 36, or a coating or material placed thereon (not shown), may function as a solid-phase support for binding reagents or other reagents. Such a configuration allows especially efficient enhancement of the rate of mass transport of reagents to and from the solid-phase support. In another alternate embodiment, the surface of reaction enclosure 34 functions as a solid-phase support for binding reagents or other reagents.

It is preferred that sonication device 36 comprises a piezoelectric sonication device. Device 36 is preferably controlled by a sonication controller (not shown) such as an electrical control circuit or the like.

Device 36 mounts on device mount 38, which is coupled to base 32. Much like device 36, device mount 38 preferably may be exposed directly to reagents 35. Alternatively, device mount is encased in a protective covering (not shown). Device mount may transmit sonication energy from device 36 to reaction enclosure 34 through base 32. Alternatively, device mount 38 is a shock-absorbing substance that minimizes the transmission of sonication energy from sonication device 36 to base 32.

Although device 36 is shown immediately abutting device mount 38, a small space may exist between device mount 38 and device 36 that allows device 36 to expand and contract or to otherwise move during sonication.

In operation, reagents 35 are introduced into reaction enclosure 34. Sonication device 36 is energized and directly sonicates reagents 35. Depending upon the composition of device mount 38, sonication energy may also be transmitted to base 32 which conducts such energy to reaction enclosure 34, and thus to reagents 35 contained therein. Alternatively, device mount 38 may transmit sonication energy to reagents 35. The sonication energy causes reagents 35 to mix, speeding the rate of reaction among reagents 35. Where enclosure 34 includes binding reagents or other reagents located at a solid-phase support, the sonication energy may also increase the rate of mass-transport of reagents to and from the support, thus, speeding the rate of binding reactions on the solid-phase support.

In certain applications it may be beneficial to prevent the transmission of sonication energy from the reaction enclosure to the main body of the cell, thus preventing the dissipation of sonication energy. Such isolation is particularly useful when the sonication generator is coupled directly to reaction enclosure 34; to a component of enclosure 34, such as a solid-phase support coupled to the enclosure; or to reagents within enclosure 34.

Figure 4:
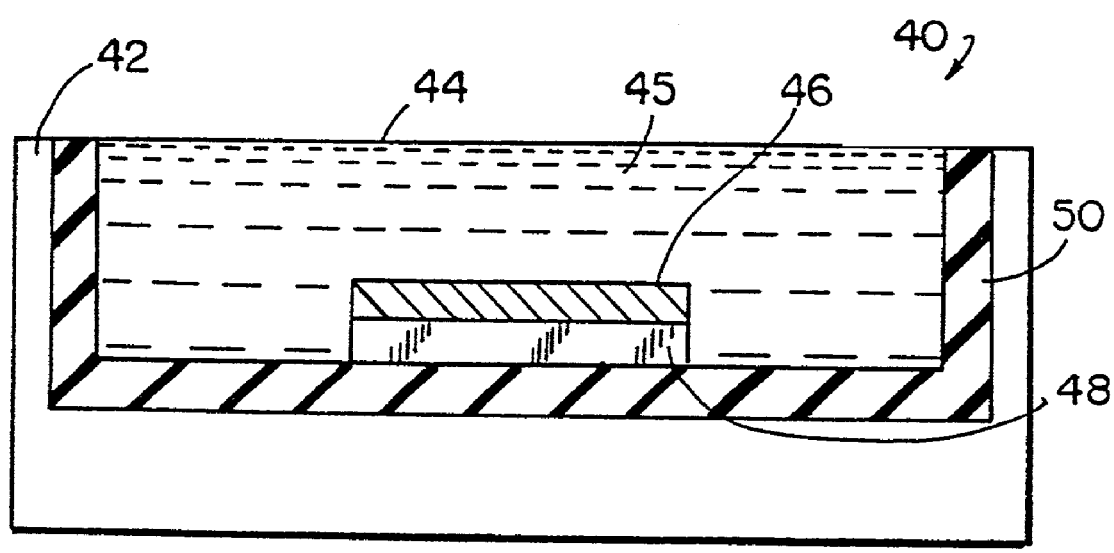
FIG. 4 is a schematic diagram of an assay cell according to yet another embodiment of the present invention.

FIG. 4 illustrates a particular cross-sectional view of an assay cell 40 according to an embodiment of the present invention. Assay cell 40 includes a base 42, a reaction enclosure 44, a sonication device 46, a device mount 48, and a sonication isolator 50. Base 42 comprises a conventional support material. Reaction enclosure 44 preferably comprises a transparent material and is coupled to sonication isolator 50.

Sonication device 46 is a device for sonicating reaction enclosure 44. Preferably, sonication device 46 may be exposed directly to reagents 45. Alternatively, sonication device 46 may be encased in a protective covering (not shown) that is capable of transmitting sonication energy from device 46 to reagents 45. Sonication device 46, or a coating or material placed thereon (not shown), may function as a solid-phase support for binding reagents or other reagents. Such a configuration especially efficiently enhances the rate of mass transport of reagents to and from the solid-phase support. In another alternate embodiment, the surface of reaction enclosure 44 functions as a solid-phase support for binding reagents or other reagents.

It is preferred that sonication device 46 comprises a piezoelectric sonication device. Device 36 is preferably controlled by a sonication device controller (not shown) such as an electrical control circuit or the like.

Device 46 mounts on device mount 48 which is coupled to sonication isolator 50. Much like device 46, device mount 48 preferably may be exposed directly to reagents 45. Alternatively, device mount 48 is encased in a protective covering (not shown). Preferably, device mount 48 is a shock-absorbing substance that minimizes the transmission of sonication energy from sonication device 46 to sonication isolator 50. Optionally, device mount 48 may be omitted entirely.

Sonication isolator 50 is preferably comprises a shock-absorbing substance that minimizes the transmission of sonication energy from sonication device 46 and mount 48 to base 42. Sonication isolator 50 can be advantageously used to decrease the emission of acoustic noise from the cell.

Although device 46 is shown immediately abutting device mount 48, a small space may exist between device mount 48 and device 46 that allows device 46 to expand and contract or to otherwise move during sonication.

In operation, reagents 45 are introduced into reaction enclosure 44. Sonication device 46 is energized and directly sonicates reagents 45. The sonication causes reagents 45 to mix, speeding the rate of reaction among reagents 45. Where enclosure includes binding reagents or other reagents located at a solid-phase support, the sonication may also increase the rate of mass-transport of reagents to and from the support, thus, speeding the rate of binding reactions on the solid-phase support.

Figure 5:
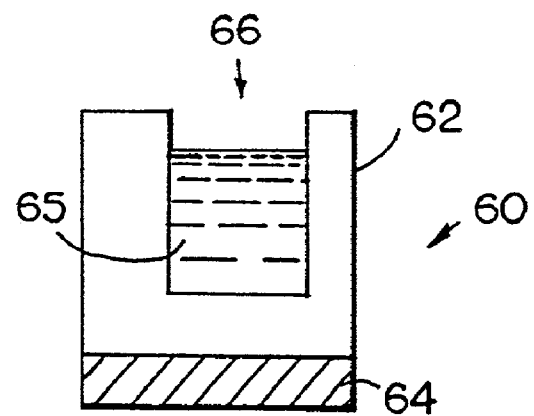
FIG. 5 is a schematic diagram of an assay cell according to still another embodiment of the present invention.

FIG. 5 illustrates a particular cross-sectional view of an assay cell 60. Assay cell 60 includes a base 62 and a sonication device 64. Preferably, base 62 comprises a rigid material. A well 66 in base 62 contains assay reagents 65. The inner surface of well 66 may function as a solid-phase support for reagents, such as binding reagents. In particular, a bottom interior surface of well 66 may comprise a solid-phase support material. Assay cells in the form of wells comprising electroactive solid-phase supports, e.g., fibril-plastic composite electrodes, for use in ECL assays are described in copending U.S. application Ser. No. 08/932,110 filed on even date herewith, and PCT Application No. PCT/US97/16942 (WO 98/12539) filed on even date herewith, both of which are incorporated by reference above.

Sonication device 64 is a device for sonicating well 66 and is structurally coupled to a bottom surface of well 66. It is preferred that sonication device 64 comprises a piezoelectric sonication device. Device 64 is preferably controlled by a sonication controller (not shown) such as an electrical control circuit or the like. In an alternate embodiment, sonication device 64 is attached to a probe (not shown) that is inserted into well 66 during an assay procedure.

In operation, reagents 65 are introduced into well 66 and sonication device 64 is energized to directly sonicate reagents 65 via structural coupling through base 62. The sonication causes reagents 65 to mix, speeding the rate of reaction among reagents 65. Under circumstances where well 66 holds binding reagents or other reagents located at a solid-phase support, the sonication may also increase the rate of mass-transport of reagents to and from the support, thus, speeding the rate of binding reactions at the solid-phase support.

In an alternate embodiment, assay cell 60 includes a plurality of wells 66 (not shown). Preferably, such wells are arranged in a conventional format, such as in a 96 or 384 well plate or the like.

Figure 6:
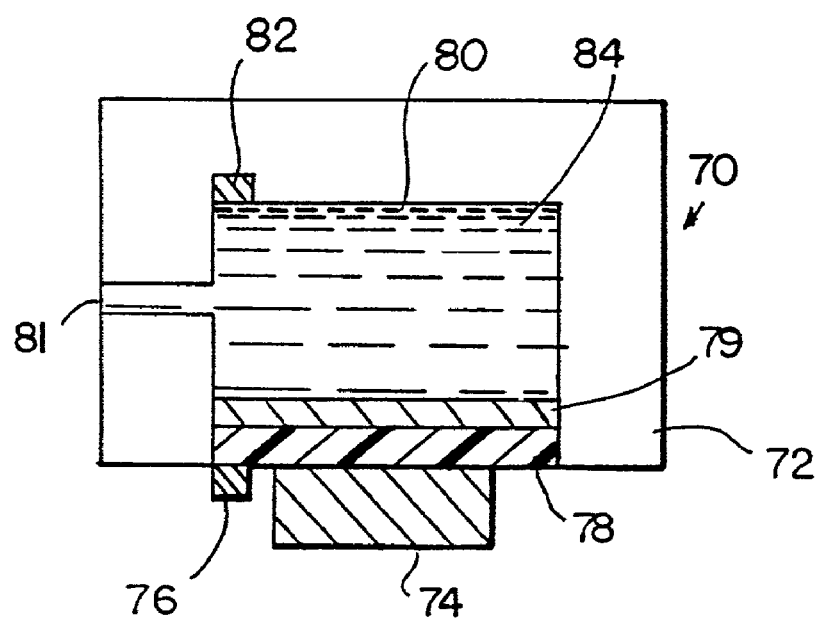
FIG. 6 is a schematic diagram of an assay cell according to another embodiment of the present invention.

FIG. 6 illustrates a particular cross-sectional view of an assay cell 70 especially adapted for conducting ECL assays. Assay cell 70 includes a base 72, a sonication device 74, an electrical contact 76, a solid-phase support 78, a reaction enclosure 80, and an electrode 82.

Base 72 is preferably a rigid material shaped to define a reaction enclosure 80 and a passage 81. Alternatively, base 72 is a flexible material (e.g. a thin plastic container or a blister-pack). Preferably, solid-phase support 78 forms a seal against base 72. Support 78 and/or base 72 may also include one or more additional passages (not shown) through which reagents may be introduced or removed. In assays that utilize optical detection techniques, e.g., ECL, fluorescence, and chemiluminescence, base 72 is preferably a transparent material, such as acrylic or the like, that allows light generated within reaction enclosure 80 to be detected by a detector (not shown) coupled to base 72. Base 72 may, alternatively, include a transparent window (not shown). Optionally, passage 81 may be omitted.

Sonication device 74 is a device for sonicating support and is structurally coupled to solid-phase support 78. It is preferred that sonication device 74 comprises a piezoelectric sonication device. Device 74 is preferably controlled by a sonication controller (not shown) such as an electrical control circuit or the like. In an alternate embodiment, sonication device 74 may also be coupled to base 72.

Electrical contact 76 is an electrically conductive material coupled to solid-phase support 78. In ECL and other electrochemical assays, electrical energy is supplied to solid-phase support 78 (working electrode) via electrical contact 76. Alternately, electrical contact 76 is a metal contact on sonication device 74 and device 74 is an electrically conductive material coupled to support 78. Similarly, electrode 82 (counter electrode) comprises electrically conductive material coupled to reagents 84.

Solid-phase support 78 supports reagents 79, such as binding reagents. In ECL assays, solid-phase support 78 preferably functions as an electrode for inducing ECL among reagents 79 and/or reagents 84. In an especially preferred embodiment, solid-phase support 78 comprises a fibril-polymer composite electrode. Preferably, solid-phase support 78 is mounted such that the transmission of sonication energy from device 74 to base 72 is minimized. Alternatively, support 78 may be mounted so that support 78 transmits sonication energy from device 74 via base 72 to the entire surface of reaction enclosure 80. Support 78 and electrode 82 are preferably coupled to a power supply (not shown) to create an electrochemical cell. Assay cell 70 may additionally include a reference electrode (not shown) which is in electrical contact with reagents 84.

Although device 74 is shown immediately abutting support 78, a small space may exist between device 74 and support that allows device 74 to expand and contract or to otherwise move during sonication.

Reaction enclosure 80 is preferably a void in base 72 in which reagents 84 may be introduced and subjected to sonication to promote mixing and reaction. Alternatively, reaction enclosure 80 may comprise a separate enclosure, preferably comprising transparent material, coupled to base 72.

In operation, reagents 84 are introduced into reaction enclosure 80, preferably via passage 81. Sonication device 74 is energized and directly sonicates support 78 which transmits such energy to reagents 84. Depending upon the mounting of support 78, sonication energy may also be transmitted to base 72 which conducts such energy to reaction enclosure 80, and thus to reagents 84. The sonication causes reagents 84 to mix, speeding the rate of reaction among reagents 84 and the rate of mass transfer of reagents 84 to and from reagents 79 on support 78.

An exemplary embodiment of a binding assay utilizing cell 70 in an ECL detection system is described in the following. Reagents 84, including an electrochemiluminescent moiety, e.g., linked to an analyte or to the binding partner of an analyte, are introduced into enclosure 80. The presence of an analyte of interest in sample reagents 84 will lead to increased or decreased binding (directly or indirectly) of the electrochemiluminescent moiety to reagents 79 on support 78. Sonication energy supplied by device 74 significantly increases the rate of mass transfer of reagents 84 to support 78 and reagents 79 thereon, thereby increasing the rate of binding reactions between reagents 79 and 84 and decreasing the time required to make an ECL measurement. Electrical energy is applied to support 78 to cause the electrochemiluminescent moiety to luminesce. The light produced by the ECL reaction may be measured while sonication device 74 operates or thereafter.

In another alternative embodiment, a dry reagent (not shown) is prestored in reaction enclosure 80 and liquid reagents are introduced into reaction enclosure 80 to directly contact said dry reagent. Upon activation of sonication device 74, the dry reagent and liquid reagents 84 intermix at a significantly faster rate than would occur in the absence of sonication. The intermixed reagents may react, e.g., with each other and/or with reagents 79 on a solid-phase support, or other reagents may then be added to the mixture and also intermixed and allowed to react.

It has been noted that the interior surfaces of reaction enclosure 80 may become coated with a substance (not shown) that interferes with a desired assay reaction. This interfering substance may include a contaminant, cellular debris, a non-specifically bound reagent, a reaction byproduct, or the like. In yet another embodiment of the present invention, sonication device 74 is activated to remove such an interfering substance from reaction enclosure 80. Sonication energy provided by sonication device 74 is transmitted to enclosure 80 and is utilized to remove the interfering substances from the interior surfaces of enclosure 80. Sonication increases the rate of mass transport at the surfaces.

As an example, an ECL assay process involving binding reactions at an electroactive solid-phase support 78 may include a cleaning cycle involving activation of device 74 before and/or after a binding reaction to properly prepare support 78 (working electrode) and/or electrodes 82 (counter electrode) for electrical inducement of ECL. Such a cleaning cycle may involve the addition of a cleaning solution to reaction enclosure 80.

As will be apparent to one of ordinary skill, assay cell 70 is also advantageously employed in non-ECL based assays, especially binding assays. Components of cell 70 related to the electrochemical excitation of ECL labels may be omitted from cell or remain unused in connection with assays that do not require electrochemical reactions. Similarly, some detection techniques may require the addition to cell 70 of technique-specific components, e.g., a light source for fluorescence or colorimetric measurements.

An instrument for conducting ECL assays that includes cell 70 may also include, but is not limited to, one or more of the following: a source of electrical energy (e.g., a potentiostat, a current source or a voltage source) for applying potentials or currents between the working and counter electrodes; a source of electrical energy (e.g., a battery) along with associated electronics for driving sonication device 74; a device for measuring light (e.g., a photomultiplier tube, one or more photodiodes, or CCD camera) generated within enclosure 80 or imaging the contents of enclosure 80; means for sample handling and processing; a microprocessor for system control, assay data gathering, and assay data analysis; and apparatus for introducing reagent samples and additional reagents and removing waste from enclosure 80.

Figure 7:
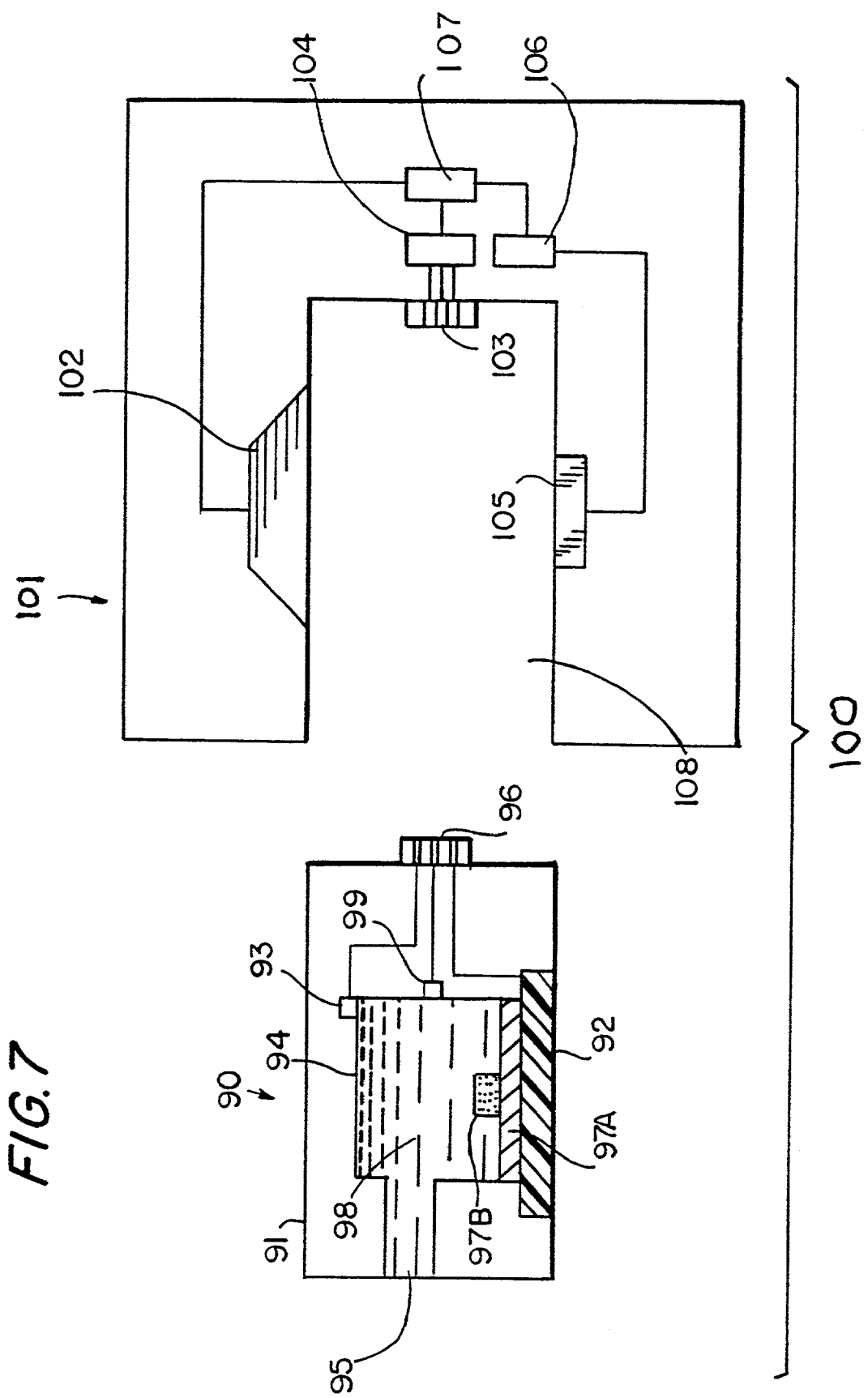
FIG. 7 is a schematic diagram of an assay system according to another embodiment of the present invention.

In still another alternate embodiment, sonication device 74 is removably and/or reversibly coupled to contact 76. Base 72, electrode contact 76, support 78, enclosure 80 and electrode 82 may together comprise a separate, disposable assay cell device. An assay system 100 for conducting ECL assays in a disposable cartridge 90 with an instrument 101 is illustrated in FIG. 7. Cartridge 90 includes a base 91, a diaphragm 92, a counterelectrode 93, a reaction enclosure 94, a sample port 95, electrical leads 96, and a reference electrode 99. Instrument 101 includes a cartridge receptacle 108, a light detector and/or imaging device 102, an electrical connector 103, a source of electrical energy for applying a voltage or current between the working and counter electrodes 104; a sonication device 105; a source of electrical energy 106 for driving sonication device 105; and a microprocessor 107 for instrument control, assay data gathering, and assay data analysis.

Diaphragm 92 is an electrically conductive solid-phase support for reagents 97A, such as binding reagents, and functions as a working electrode. In a preferred embodiment, diaphragm 92 is a fibril-polymer composite electrode and reagents 97A comprise binding reagents such as antibodies, nucleic acids, receptors, etc. immobilized thereon. In an especially preferred embodiment, binding reagents specific for a variety of analytes are patterned into binding domains on diaphragm 92. Base 91 is preferably a rigid and transparent material, such as acrylic or the like, that allows light generated by an ECL reaction occurring within enclosure 94 to be detected by detector 102. Base 91 is shaped to define reaction enclosure 94 and sample port 95. Diaphragm 92 is preferably sealed to base 91.

Electrical leads 96 are electrical contacts providing electrical coupling to diaphragm 92, to counter electrode 93, and to reference electrode 99. Preferably, diaphragm 92 is mounted such that the transmission of sonication energy from device 105 to base 91 is minimized. Alternatively, diaphragm 92 may be mounted so that diaphragm 92 transmits sonication energy from device 105 to base 91, and thereon to the entire surface of reaction enclosure 94.

Preferably, reaction enclosure 94 is partially defined by the inner surface of base 91. Alternatively, reaction enclosure 94 may comprise a separate enclosure made of a transparent material which couples to base 91.

Counter electrode 93 is preferably an electrically conductive material, such as metal. Reference electrode 99 is preferably an Ag/AgCl reference electrode. Electrodes 93 and 99 are located within base 91, are coupled to leads 96, and are adapted to be in electrical contact with reagents 98. Optionally, reference electrode 98 may be omitted. Aperture 95 is preferably adapted for insertion of sample material (e.g., reagents 98) via a small tube (not shown), such as a capillary tube.

The inner surface of instrument 101 is adapted to receive and align cartridge 90 and its components with receptacle 108 and its counterpart components, including sonication device 105, electrical connections 103 and detector 102. Preferably, detector 102 is an array of detectors (e.g., a CCD camera or a photodiode array) that can image the light emitted during an ECL reaction at the working electrode. Detector 102 may be a single detector such as a photomultiplier tube, a photodiode, or the like. Insertion of cartridge 90 in instrument 101 aligns detector 102 with base 91 such that detector 102 is positioned to detect much of the light produced within enclosure 94.

Sonication device 105 is a device for sonicating diaphragm 92 which transmits the sonication energy to reagents 98 contained in reaction enclosure 94. Insertion of cartridge 90 in instrument 101 preferably aligns device 105 with the center of diaphragm 92 such that device 105 may be moved into contact with diaphragm 92. Insertion of cartridge 90 in instrument 101 causes sonication device 105 to be structurally coupled to diaphragm 92. It is preferred that sonication device 105 comprises a piezoelectric sonication device that may include a piston. Preferably, sonication device 105 is movable to achieve contact with diaphragm 92 when cartridge 90 is inserted into instrument 101.

Upon insertion of cartridge 90 into receptacle 108, electrical leads 96 are coupled to electrical connections 103. The source of electrical energy 104 may be a controllable voltage or current source adapted for control by microprocessor 107. Alternatively, if cartridge 90 includes a reference electrode, source 104 is preferably a potentiostat.

Controlled energy source 106 is preferably a conventional controllable electronic circuit driving device for controlling the operation of sonication device 105. Operation of source 106 is controlled by microprocessor 107. Microprocessor 107 is a conventional processor device, such as a software-programmed microprocessor, a microcontroller, or the like. Microprocessor 107 controls the operation of detector 102 and energy sources 104 and 106, and receives intensity data from detector 102 along with voltage and/or current data from source 104. Preferably, microprocessor 107 is additionally capable of processing the assay data and providing a corresponding output to a user and/or to another device.

In operation, a sample comprising reagents 98 is introduced via sample inlet port 95 into reaction enclosure 94. The reagents required for conducting an ECL assay may already have been added to the sample. Said reagents include: ECL coreagents (e.g., tripropylamine), ECL moieties (e.g., Ru(II) (bpy)3 or derivatives, preferably linked to an analyte or the binding partner of an analyte), blocking agents (e.g., BSA), buffers, excipients, additives, preservatives and the like. In a preferred embodiment, the cartridge is prestored with some or all of the reagents required to conduct an assay, shown as reagents 97B. In an especially preferred embodiment, reagents 97B are stored in a dry form within reaction enclosure 94.

To conduct an assay, cartridge 90 is placed in instrument 101, sonication device 105 is structurally coupled to diaphragm 92, and device 105 activated by source 106 to sonicate diaphragm 92. Sonication energy is then transmitted through diaphragm 92 to reagents 98. Depending upon the mounting of diaphragm 92, sonication energy may also be transmitted to base 91 which will conduct such energy to reaction enclosure 94, and thus to reagents 98.

The sonication causes reagents 98 and reagents 97B to mix, speeding the rate of reaction among components reagents 98 and/or 97B and the rate of mass transfer of reagents 98 and/or 97B to and from diaphragm 92. Sonication energy from device 105 significantly increases the rate of mass transfer of reagents 98 and/or 97B to support 92, thereby increasing the rate of binding reactions between reagents 97A and components of reagents 97B and 98, and decreasing the time required to make an ECL measurement. Electrical energy is applied to diaphragm 92 and to electrodes 93, by source 104 via connector 103 and leads 96, to cause an electrochemiluminescent moiety in reactants 97A, 97B and/or 98 to luminesce. The light produced by the ECL reaction may be measured (or imaged) while sonication device 105 operates or thereafter.

Microprocessor 107 controls the operation of sources 104 and 106 and receives intensity data from detector 102 along with voltage and/or current data from source 104. Microprocessor 107 analyzes, and may store, the received data and preferably produces a corresponding output for provision to a user or to another device (not shown). Preferably, upon completion of data collection, microprocessor 107 notifies the user that cartridge may be removed from instrument 101. Upon receiving such notification from microprocessor 107, or otherwise determining that assay data collection is complete, the cartridge 90 is removed from device 101 and suitably disposed of or recycled.

In an alternate embodiment of system 100, that portion of leads 96 coupled to diaphragm 92 is omitted and an electrical connection is added between source 104 and sonication device 105. Accordingly, the corresponding connection of connector 103 may also be omitted. In this embodiment, sonication device 105 functions as the electrical connection to diaphragm 92. When cartridge 90 is inserted into instrument 101, electrical energy is provided through sonication device 105 to reagents 98 via diaphragm 92. Such application of electrical energy may or may not be simultaneous with the application of sonication energy.

In an alternate embodiment, diaphragm 92 and/or enclosure 94 are pre-coated with a reagent or the like. Sonication of electrode 92 may cause such reagent to loosen, allowing the reagent to mix with reagents 98 within enclosure 94.

In another alternative embodiment, a dry reagent 97B is prestored in reaction enclosure 94 and liquid reagents 98 are introduced into reaction enclosure 94 to directly contact dry reagent 97B. Upon activation of sonication device 105, dry reagent 97B and liquid reagent 98 intermix at a significantly faster rate than in the absence of sonication energy. The intermixed reagents may react e.g., with each other and/or with reagents on a solid-phase support 92, or another reagent may then be added and also intermixed. In a different embodiment, reagent 97B is omitted.

The interior surfaces of reaction enclosure 94 may become coated with a substance that interferes with an assay. This interfering substance may include a contaminant, cellular debris, a non-specifically bound reagent, a reaction byproduct, or the like. In yet another embodiment of the invention, sonication device 105 is activated and the sonication energy removes the interfering substances from the interior surfaces of enclosure 94 by sonicating such substances to loosen or by causing increasing the rate of mass transport at the surfaces. For example, an ECL assay may use cleaning cycles involving activation of device 105 before and/or after the binding reaction to properly prepare the electrode for the excitation of ECL. These cleaning cycles may involve adding to reaction enclosure 94 a cleaning solution which assists in loosening such interfering substances.

In still another alternate embodiment, sonication device 105 and source 106 are omitted from instrument 101 and diaphragm 92 additionally comprises a sonication device like device 105. Further, source 104 incorporates the functionality of source 106. Electrical power from source 104 to activate the sonication device of diaphragm 92 is conducted via connector 103 and leads 96.

In continuous or intermittent ECL measurements, the rate of a binding reaction is measured continuously or at intermittent intervals. A description of this process is found in U.S. Pat. No. 5,527,710 (Nacamulli et al.). The present invention will act to increase the rate of binding reactions in such assays, and will also provide reproducible mixing so as to provide precise and reproducible rate measurements. Sonication may also be continuous or intermittent during such assays. An advantage of continuous or intermittent measurements for determining the rate of a binding reaction is that it offers increased sensitivity and precision as compared to single-point ECL measurements.

EXAMPLES

Example 1

Preparation of Fibril-Plastic Composites

Composite plastic materials comprising carbon fibrils in a polymer matrix were prepared by methods analogous to those described in copending U.S. application Ser. No. 08/932,110 filed on even date herewith, and PCT Application No. PCT/US97/16942 (WO 98/12539) filed on even date herewith, both of which are incorporated by reference above. To give a better understanding of the following examples, a brief description of the steps for preparing the composites used in the examples is provided. Carbon fibrils (Hyperion Catalysis) were compounded with poly(ethylene-co-vinyl acetate) (EVA) and the resulting composite material was extruded into sheets. The sheets were oxidized with chromic acid to expose carbon fibrils near the surface and to introduce carboxylic acid groups. Protein was immobilized on the composite by activation of the carboxylic acid groups with ethyl-dimethylpropyl-carbodiimide (EDC) in the presence of N-hydroxysuccinimide (NHS) followed by treatment with the protein in a slightly basic buffered solution. In an alternate procedure, proteins were immobilized by non-covalent adsorption on composite sheets that had been treated with a plasma formed from water-saturated argon.

Example 2

Increasing the Rates of Binding Reactions at a Solid-Phase Support with Sonication: Use of a Low-Power Piezoelectric Buzzer Streptavidin was immobilized onto chromic acid-oxidized EVA-fibril composite as described in Example 1. A 5/16 inch diameter disc cut from this material was placed in the well formed by placing a gasket on a low-power low-frequency acoustic piezoelectric transducer. Treatment of the disc with a solution containing a biotin-labeled α-Fetoprotein (anti-AFP) antibody (Boeringer-Mannheim, 50 uL, 41 nM) led to immobilization of the antibody. The binding reaction was essentially complete in 3 minutes upon sonication by the piezoelectric transducer. The extent of the reaction was determined using a biotin- and TAG1-labeled antibody and measuring bound antibody by ECL. The same reaction took more than 20 minutes when mass-transport occurred through diffusion alone that is, without sonication.

Figure 8:
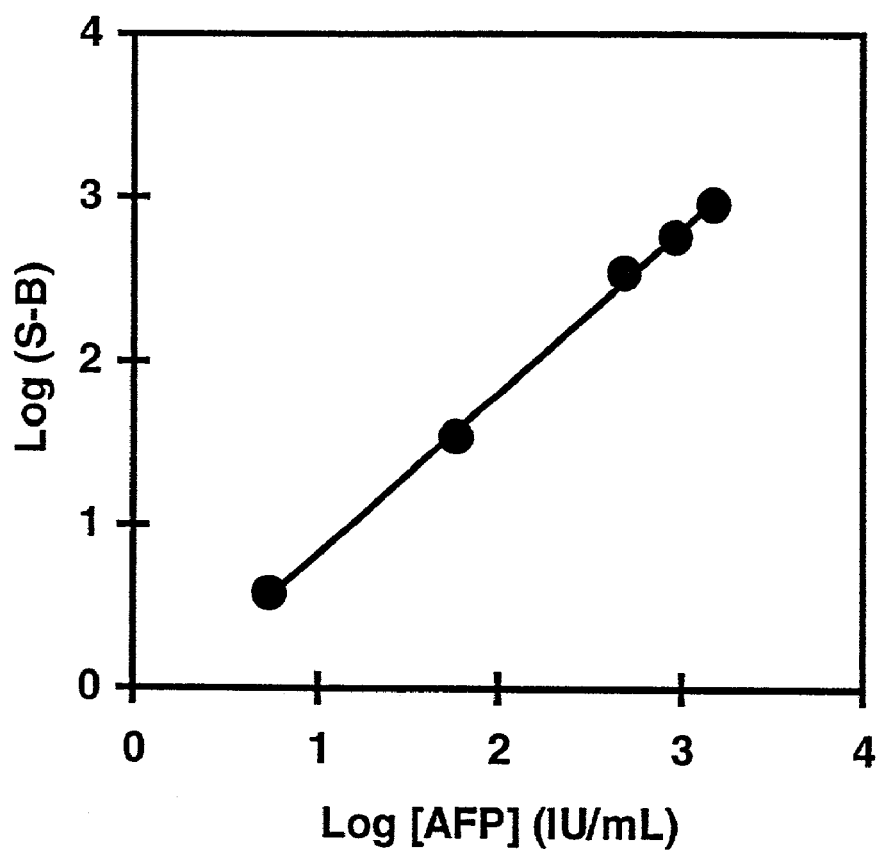
FIG. 8 is a graph illustrating ECL intensity results obtainable according t o the present invention.

The antibody-coated composite was washed with 50 mM phosphate, pH 7.5. To assay for α-Fetoprotein (AFP) in a sample, a solution containing a TAG1-labeled secondary antibody directed against AFP (Boeringer-Mannheim, 50 uL, 12 ug/mL) followed by the sample (10 uL) were added to the well. The piezoelectric transducer was used to sonicate the composite and solution for a period of 5 minutes. The disc was washed with phosphate buffer and placed in an electrochemical cell designed for measuring ECL. The cell was filled with ORIGEN Assay Buffer (IGEN, International) and the potential of the composite was scanned from 0 to −0.8 to 1.2 V (vs. Ag/AgCl) at a scan rate of 100 mV/s. The difference between the integrated ECL signal (S) obtained for samples containing known concentrations of AFP and the background signal (B) determined for in the absence of AFP is shown in FIG. 8 where the signals are provided using a relative scale of intensity). The rate of formation of the sandwich complex was 3–4 times faster when sonication energy was applied (piezoelectric transducer "on") as opposed to when sonication energy was not applied (transducer "off"). Similar results were obtained using a piezoelectric transducer that operated in the ultrasonic frequency range.

Example 3

Increasing the Rates of Binding Reactions at a Solid-Phase Support with Sonication: Use of an ECL Cell Instrument with an Integrated Piezoelectric Sonication Device EVA-fibril composite was treated with a water-saturated argon plasma and coated with an anti-AFP antibody (Boeringer-Mannheim) as described in Example 1. A 10×15 mm rectangle of the composite was placed in an ECL cell (see FIG. 6).

Figure 9:
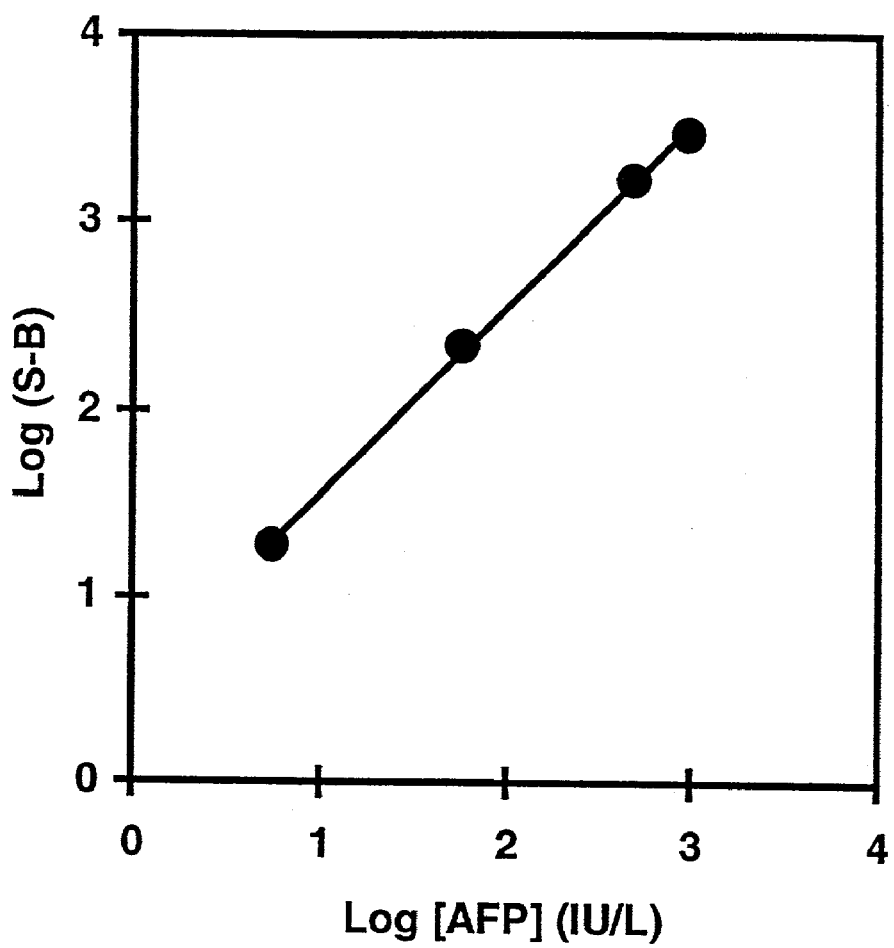
FIG. 9 is another graph illustrating ECL intensity results obtainable according to the present invention.

The sample (10 uL) and a solution containing a TAG1-labeled anti-AFP antibody (Boeringer-Mannheim, 50 uL, 12 ug/mL) were combined and introduced into the cell. The binding reaction was allowed to proceed for 3 minutes during which time a piezoelectric transducer (sonication generator) was driven at its resonance frequency (47 KHz) at a power of approximately 2.5 W. The transducer was turned off, the cell was flushed with ORIGEN Assay Buffer (IGEN, International), and the voltage at the composite was ramped from 0 to −0.8 to 1.2 V (vs. Ag/AgCl) at a rate of 0.1 V/s. The difference between the integrated ECL signal (S) obtained for samples containing known concentrations of AFP and the background signal (B) determined for in the absence of AFP is shown in FIG. 9 (where the signals are provided using a relative scale of intensity). The assay demonstrated a dynamic range of greater than three orders of magnitude and precision of ±5% or better.

Example 4

The Binding Kinetics for Formation of a Sandwich Immunocomplex on a Solid-Phase Support: The Effect of Sonication on an AFP Assay The kinetics of the binding reaction of the AFP assay described in Example 3 were determined by varying the incubation time allowed for the formation of the sandwich immunocomplex on the composite. A sample containing AFP at a concentration of 59 IU/mL was used in these experiments. Two sets of experiments were conducted. In one set of experiments sonication energy was applied (the piezoelectric transducer was activated) during the incubation time for the binding reactions, while in the other set, sonication energy was not applied (the piezoelectric transducer was not activated).

Figure 10:
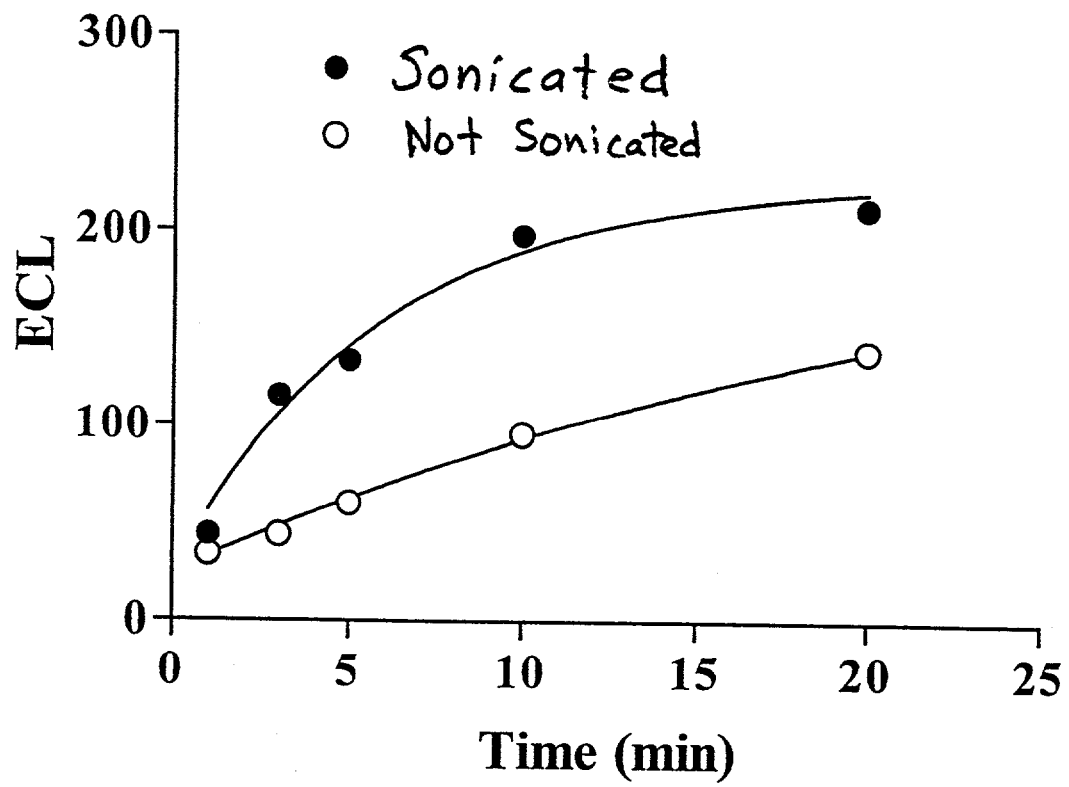
FIG. 10 is a graph illustrating the improvement in ECL intensity results obtainable according to the present invention.

FIG. 10 shows the intensity of the ECL (on a relative intensity scale) that was measured as a function of the time allowed for the formation of the immunocomplex. The measured ECL signal (for a given incubation time) was larger for those samples that had sonication energy applied during the incubation period than for those samples that did not. Since the magnitude of the measured ECL signal increases with increased binding (to form more sandwich immunocomplexes), these results clearly show that sonication of the assay significantly increases the rate of the binding reactions. Using the slope of the line connecting the first two points as a rough indication of the rate of binding, the rate enhancement attributable to sonication was greater than a factor of 7. The plot also shows that the three-minute assay described in Example 3 is a kinetic assay (in that period of time the binding is approximately one-third to one-half complete); after 10 minutes, the reaction is essentially complete.

Example 5

Use of Piezoelectric Transducer to Increase the Rate of Mass Transport to and/or from an Electrode During an Electrochemical Reaction: Sonication of Fibril-EVA Composite Electrodes During the Excitation of ECL An untreated EVA-fibril composite electrode was placed in the ECL cell described in Example 3. The cell was filled with a 10 nM solution of Ru(II) (bpy)3 in ORIGEN Assay Buffer (IGEN, International). ECL was excited from the label by ramping the composite electrode from 0 to –0.8 to 2.3 V (vs. Ag/AgCl). The integrated ECL signal measured with a PMT in the absence of mixing was 1332 on a relative intensity scale. Under the same conditions, but with sonication (the piezoelectric transducer turned "on"), the integrated ECL signal was 3086 on a relative intensity scale. Sonication, therefore, caused ECL intensity to more than double.

Although illustrative embodiments of the present invention and modifications thereof have been described in detail herein, it is to be understood that this invention is not limited to these precise embodiments and modifications, and that other modifications and variations may be effected therein by one skilled in the art without departing from the scope and spirit of the invention as defined by the appended claims.

What is claimed is:

1. A method for conducting an electrochemiluminescence assay to detect or quantitate an analyte comprising the steps of:
    (a) introducing a composition containing an analyte of interest bound to an electrochemiluminescent moiety into a cell including a working electrode;
    (b) sonicating said composition in said cell with means structurally coupled to said cell;
    (c) applying electrical energy to said electrode to cause said electrochemiluminescent moiety to luminesce; and
    (d) detecting or quantitating the electrochemiluminescence from said cell to detect or quantitate said analyte.

2. A method for conducting a binding assay comprising:
    (a) introducing a composition into a cell, comprising (i) a solid phase support, the solid phase support having a binding reagent immobilized thereon to form a binding domain and (ii) a sonication device structurally coupled to the cell, wherein said composition comprises at least one binding component that binds to said binding reagent;
    (b) sonicating the composition in the cell with the sonication device so as to increase the rate of binding reactions at the binding domain; and
    (c) detecting or quantitating the results of the binding assay.

3. The method according to claim 2 wherein the solid phase support comprises at least one additional binding reagent immobilized thereon to form a plurality of discrete binding domains.

4. The method according to claim 2 wherein the cell comprises at least one additional solid phase support structurally coupled to the sonication device, the additional solid phase support having an additional binding reagent immobilized thereon to form an additional binding domain.

5. The method according to claim 2 wherein the solid phase support is an electrode.

6. The method according to claim 5 wherein the step of detecting or quantitating is performed using electrochemiluminescence.

7. The method according to claim 2 wherein the sonication device is a piezoelectric device.

8. The method according to claim 2 wherein the sonication device is an electromagnetic actuator.

9. The method according to claim 7 or 8 wherein the sonication device is capable of providing sonication energy at from 0.1 to 10,000 kHz.

10. The method according to claim 2, the cell further comprising thin capillaries, wherein operation of the sonication device increases the rate of fluid flow through the thin capillaries.

11. The method according to claim 2 wherein the solid phase support is structurally coupled, through a surface of the cell, to the sonication device.

12. The method according to claim 11 wherein the surface of the cell is a diaphragm.

13. A method of conducting a solid phase binding assay wherein the solid phase is structurally coupled to a sonication device, the method comprising:
    (a) contacting the solid phase, said solid phase including a binding reagent, with a composition containing at least one binding component; and
    (b) sonicating the solid phase with the sonication device so as to increase the rate of binding reaction of said binding component to said solid phase.

* * * * *